(12) United States Patent
Ohkawa

(10) Patent No.: US 6,521,210 B2
(45) Date of Patent: Feb. 18, 2003

(54) METHOD FOR IMAGING MALIGNANT TUMORS USING CARBON 13 WITH MRI

(75) Inventor: Tihiro Ohkawa, La Jolla, CA (US)

(73) Assignee: Archimedes Technology Group, Inc., San Diego, CA (US)

( * ) Notice: Subject to any disclaimer, the term of this patent is extended or adjusted under 35 U.S.C. 154(b) by 0 days.

(21) Appl. No.: 09/736,526

(22) Filed: Dec. 13, 2000

(65) Prior Publication Data

US 2002/0071808 A1 Jun. 13, 2002

(51) Int. Cl.$^7$ .......................... A61B 5/055; G01N 24/00
(52) U.S. Cl. ........................................ 424/9.3; 436/173
(58) Field of Search ............................ 424/9.3, 9.341, 424/9.1, 1.81; 436/173

(56) References Cited

U.S. PATENT DOCUMENTS

| | | |
|---|---|---|
| 4,498,048 A | 2/1985 | Lee |
| 4,673,882 A | 6/1987 | Buford |
| 4,766,378 A | 8/1988 | Danby |
| 4,829,252 A | 5/1989 | Kaufman |
| 5,061,897 A | 10/1991 | Danby |
| 5,124,651 A | 6/1992 | Danby |
| 5,184,074 A | 2/1993 | Kaufman |
| 5,597,548 A * | 1/1997 | Sherry et al. ................. 424/9.3 |
| 6,329,208 B1 * | 12/2001 | Jones et al. .................. 436/173 |

* cited by examiner

*Primary Examiner*—Michael G. Hartley
(74) *Attorney, Agent, or Firm*—Nydegger & Associates

(57) ABSTRACT

In accordance with the present invention, a method for imaging a malignancy in a patient, in situ, requires feeding the patient a nutrient that is enriched with carbon 13 ($^{13}C$). This feeding step can be accomplished either orally or intravenously, and can last for approximately 24 hours. Magnetic Resonance Imaging (MRI) techniques are then used on the patient with rf energy that is tuned to the nuclear resonance of $^{13}C$. An image of selected tissue in the patient is thereby created, and this image is thereafter evaluated for any concentrations of $^{13}C$ that will delineate a malignancy. If present, the malignancy can then be treated. A subsequent (feeding)/(MRI imaging) procedure may be performed. The image that is created in this subsequent procedure can then be compared with the image that was created in the first procedure to determine the efficacy of the treatment, or to determine a growth rate for the malignancy.

7 Claims, 1 Drawing Sheet

FIGURE
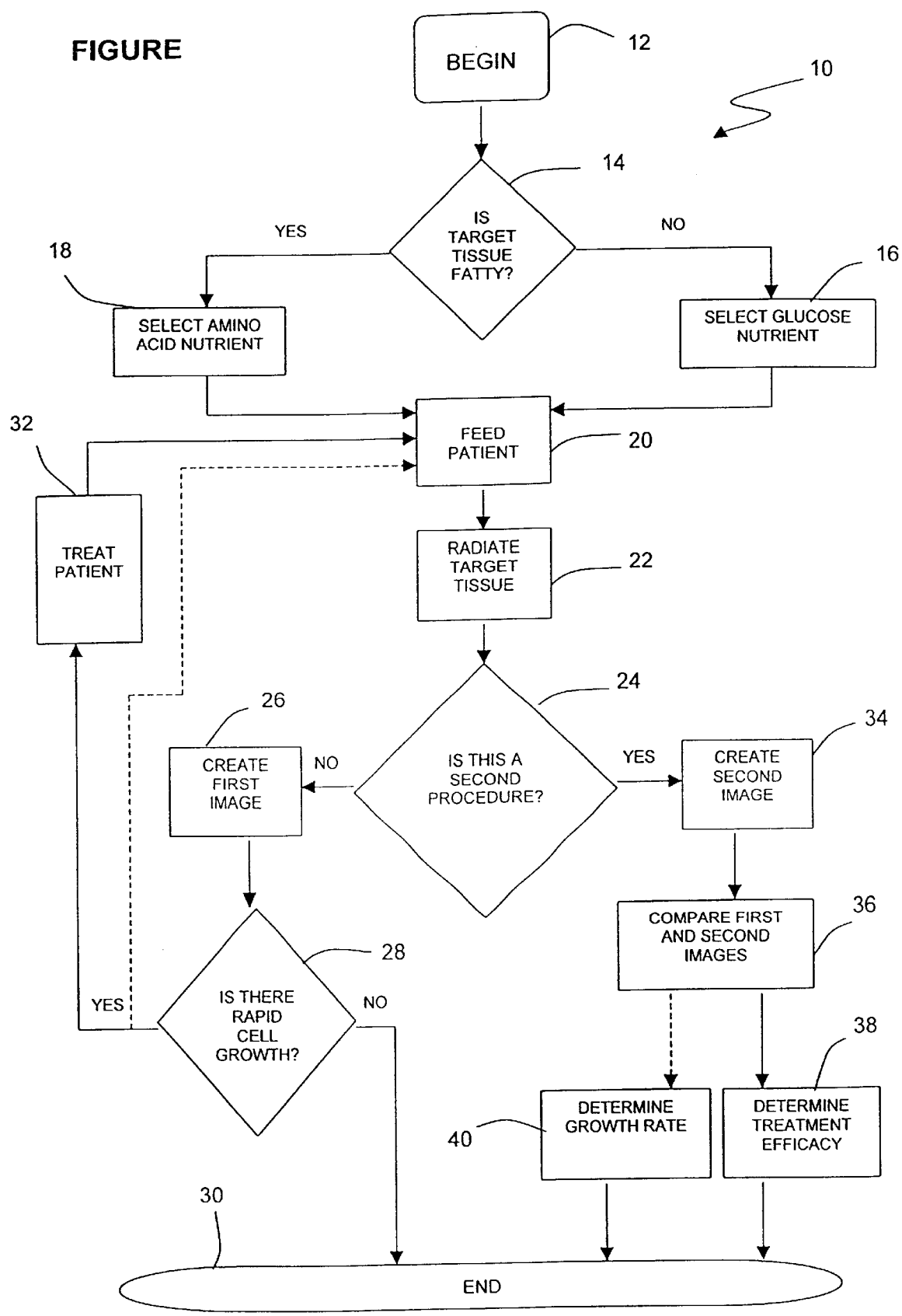

METHOD FOR IMAGING MALIGNANT TUMORS USING CARBON 13 WITH MRI

FIELD OF THE INVENTION

The present invention pertains generally to methods and systems for diagnosing a malignancy in situ tissue. More particularly, the present invention pertains to methods and systems for using carbon 13 ($^{13}C$) as a target material for detecting the presence of a malignancy in situ tissue of a patient. The present invention is particularly, but not exclusively, useful as a method and a system for using MRI techniques to image concentrations of $^{13}C$ in rapidly growing tissue.

BACKGROUND OF THE INVENTION

In normal healthy tissue, cells will grow, divide, and die in an orderly manner. In this process, normal cell division is necessary to sustain life and insure the orderly function of organs and tissues. As is well known, when cell division occurs, the result is the replication of a parent cell into daughter cells. The daughter cells then continue to function in the same way as did the parent cell. According to the type of tissue involved, however, the rate of cell division for normal cells will differ. For example, the rate of cell division in epithelial tissue and in bone marrow tissue is more rapid than is the rate of cell division in other tissues. In any event, for normal cell division, the cells of each organ will replicate at a pre-programmed rate specific to that organ. Unfortunately, however, it happens that for any number of reasons the rate of cell division may change. In some cases, this gives rise to rapidly growing cells whose rate of cell division is out of control. As we know, cancer is one consequence of such rapid cell growth, and cancer can take many forms. As we also know, undetected and untreated cancer can be fatal.

Cell division requires nutrients, regardless whether the tissue is healthy or cancerous. Importantly, carbon is an essential element in these nutrients. Indeed, all cells contain carbon, and about ninety percent of the carbon that is used by a cell can be found in its structural components, such as the cell wall and the nucleus. Further, it is known that when a cell grows and divides, the structural components of the daughter cells are synthesized from available nutrients. In fact, nearly fifty percent of the carbon from a nutrient that has been used by a parent cell can be found in each of the daughter cells.

Naturally occurring carbon is mostly in the form of the carbon 12 isotope ($^{12}C$). A small percentage of naturally occurring carbon, however, is in the form of carbon 13 ($^{13}C$). Insofar as cell division is concerned, cells metabolize carbon 13 ($^{13}C$) the same as they do the more common form of carbon, $^{12}C$. In at least one important respect, $^{12}C$ and $^{13}C$ are different. Specifically, it happens that $^{13}C$ responds particularly well to nuclear magnetic resonance, making it particularly useful for MRI techniques. Thus, by tuning the rf energy of an MRI for nuclear resonance with $^{13}C$, images can be created which react to the presence of $^{13}C$ in a tissue. Fortunately, carbon with an increased concentration of the $^{13}C$ isotope can be produced by physical and chemical means. In fact, nutrients which are highly enriched with $^{13}C$ are commercially available.

Normal cells divide at predetermined rates based on the type of tissues to which they belong. In comparison with cells of the same tissue, cancer cells divide at a much faster rate. In most cases, these rapidly dividing cancer cells may take only about 8 hours to divide. Thus, in a 24 hour period they will divide about three times. Consequently, when a patient is fed a nutrient enriched with $^{13}C$ over a twenty-four hour period, there will be a discernibly high concentration of $^{13}C$. As a practical matter, the new cells in a malignancy will be largely made of the $^{13}C$. A few hours after the feeding is interrupted, the unused portion of the enriched nutrient will have been metabolized and will disappear from the body.

A cell's use of nutrients is generally dependent on two factors. One factor is the type of tissue, i.e. is the tissue fatty or non-fatty tissue. The other factor, which is interrelated to the first factor, concerns the type of nutrient that is used by the tissue for cell division, e.g. glucose or amino acid. Thus, the composition of nutrients to be used to target specific cells will generally depend on whether the cells are fatty or non-fatty tissue.

Specifically, because nutrients will either metabolize, be used for cell division, or be stored as fat, it is desirable to select a nutrient that will either metabolize or contribute to cell division, and will not be primarily stored as fat.

Heretofore, the detection of malignancies has been accomplished in several ways, using either invasive or non-invasive methods. Invasive techniques, such as the taking of a biopsy, have been used extensively. Invasive techniques, however, can cause varying degrees of extended patient discomfort. On the other hand, non-invasive radiation techniques, such as X-ray and MRI, do not involve extended discomfort, but they have been used with mixed results. The difficulty here has been mostly in properly interpreting the form and structure of target tissue to diagnose a malignancy.

As just indicated, radiation methods for detecting malignancies have depended on an interpretation of the morphology of the tissue. For instance, to image tissue, X-ray technology depends on the density of the tissue being targeted. MRI, on the other hand, relies on the reaction of protons in the target tissue to a magnetic field, in order to image the tissue and thereby determine its morphology. Using either technique, however, when a malignancy has not grown to a size which can distinguish it from the morphology of surrounding tissue, presently used radiation techniques may be inadequate. Stated differently, presently used radiation techniques for distinguishing the morphology of a tissue have been generally unsatisfactory for detecting cancerous cells during their earliest rapid growth stages.

In light of the above, it is an object of the present invention to provide a method for the in situ imaging of a malignancy in a patient that is independent of the morphology of the tissue. Another object is to provide a method and a system for targeting cells in an in situ tissue, according to the composition of the tissue. A further object is to provide a method for the in situ imaging of a malignancy wherein a nutrient is selected to identify rapidly growing cells based upon their use of the selected nutrient in cell division. Another object is to provide a method for determining the growth rate of target cells in situ tissue. Yet another object is to provide a method and a standard for determining the efficacy of a treatment of a malignancy in a patient.

SUMMARY OF THE PREFERRED EMBODIMENTS

A system and method for identifying rapidly dividing cells in situ tissue in a patient in accordance with the present invention requires feeding the patient a nutrient enriched with $^{13}C$. According to well known functions of cellular physiology, the $^{13}C$ enriched nutrient will then be used by the cells of the in situ tissue to incorporate the $^{13}C$ into the cells that result from cell division.

Typically, the feeding of the patient extends over a period of 24 hours, and can be accomplished either orally or intravenously. Further, it is desirable to use nutrients containing glucose enriched with $^{13}C$ when the target tissue is non fatty, and to use nutrients containing amino acid enriched with $^{13}C$ when the target tissue is fatty.

After the nutrient enriched with $^{13}C$ has been assimilated by the patient, the method of the present invention envisions using well known MRI techniques for the purpose of imaging the tissue containing $^{13}C$. These MRI techniques include placing the target tissue of the patient to be imaged in a magnetic field. This portion of the patient is then radiated with rf energy that is tuned for nuclear resonance with $^{13}C$. An evaluation of the resultant image for concentrations of $^{13}C$ within the target tissue will determine whether there is rapid cell growth in the target tissue.

The system of the present invention also envisions a possible subsequent procedure, to determine the growth rate of a tumor or to evaluate treatment efficacy. Specifically, after a first procedure has been completed, and after a predetermined period of time, the patient is again fed a nutrient enriched with $^{13}C$ over a twenty-four hour period. Again, the target tissue is imaged using MRI techniques. The image thus created in the second procedure is then compared with the image that was created in the first procedure. Based on this comparison, the change in the concentration of $^{13}C$ can then be measured to determine the growth rate of the tumor. Alternatively, the comparison can be made to show an absence or presence of rapidly growing tissue to determine the efficacy of a treatment.

BRIEF DESCRIPTION OF THE DRAWINGS

The novel features of this invention, as well as the invention itself, both as to its structure and its operation, will be best understood from the accompanying drawing, taken in conjunction with the accompanying description, in which similar reference characters refer to similar parts, and in which:

The Figure is a logic diagram of the steps involved in the method of the present invention.

DESCRIPTION OF THE PREFERRED EMBODIMENT

A method for performing the steps of the present invention is shown in diagram form in the Figure and is generally designated 10. As indicated in block 12, the method 10 begins with a determination by a physician that a patient has a target tissue that may contain a possible malignancy. Once the target tissue has been identified, the inquiry diamond 14 indicates that the question is presented as to whether the target tissue is fatty. If the target tissue is non-fatty, block 16 of method 10 indicates it is necessary to use nutrients containing glucose enriched with $^{13}C$. When the tissue is fatty, however, inquiry diamond 14 is directed toward block 18 which indicates that a nutrient containing amino acids enriched with $^{13}C$ is to be selected. Upon selection of the desired nutrient, feeding the patient is initiated as indicated by block 20. The feeding step 20 is typically accomplished over a period of twenty-four hours, and can be accomplished either orally or intravenously. As indicated by block 22, at a predetermined time following the feeding (block 20), allowing for the unused portion of the of the enriched nutrient to disappear from the body, the step of radiating the target tissue is performed.

Also shown in the Figure at inquiry diamond 24, the inquiry is made as to whether this is a second procedure. Accordingly, if the answer to this inquiry 24 is no, a first image is created as indicated by block 26. Specifically the present invention requires imaging with an MRI that is tuned for nuclear resonance with $^{13}C$. Creation of the first image (block 26) is followed by another inquiry, block 28, regarding the presence of rapid cell growth as delineated in the first image. If the answer to the inquiry (diamond 28) regarding the presence of rapid cell growth is "no," the method 10 is concluded, as indicated by the oval 30 marked "End." If, on the other hand, the answer to the inquiry (diamond 28) regarding rapid cell growth is "yes," a subsequent procedure is performed.

Depending on the information desired, if it is determined that rapid cell growth is present (inquiry diamond 28), the patient may be treated for the malignancy, as indicated by block 32. According to the parameters of a given treatment, after treating the patient (block 32), the steps of the first procedure are repeated. These steps are namely feeding the patient a nutrient enriched with $^{13}C$ (block 20) and radiating the target tissue (block 22). Upon completion of the radiation of the target tissue (block 22), the determination is again made concerning whether this is a second procedure (inquiry diamond 24). The answer to this inquiry for a subsequent procedure will be "yes," and as indicated by block 34, a second image will be created. The first image and the second image are then compared (block 36), to determine the treatment efficacy (block 38). As shown in the Figure, this could end the process (oval 30).

It is also envisioned by the method 10 of the present invention, that it may be desirable to ascertain the growth rate of the malignancy. In this case, upon receiving a positive response for inquiry diamond 28, the method 10 will conduct a subsequent procedure. This subsequent procedure requires the steps of feeding the patient a nutrient enriched with $^{13}C$ (block 20) and radiating the target tissue (block 22). Once again, the answer of inquiry diamond 24 will be "yes," and as indicated by block 34, a second image is created. Following the creation of the second image (block 34) the first and second images are compared (block 36). As shown in the Figure at block 40, the growth rate can then be determined and the process will have reached the end, indicated by oval 30.

While the particular method for imaging in situ imaging malignant tumors using carbon 13 with MRI as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for identifying rapidly dividing cells of a malignancy in situ tissue of a patient which comprises the steps of:

providing a nutrient enriched with $^{13}C$;

administering said nutrient to the patient for use by in situ tissue during cell division to incorporate said $^{13}C$ into cells of the in situ tissue;

positioning the in situ tissue in a magnetic field;

radiating the in situ tissue in the magnetic field with rf energy, the rf energy being tuned for nuclear resonance with $^{13}C$ to create an image of the in situ tissue; and evaluating the image for concentrations of $^{13}C$ therein to identify the rapidly dividing cells.

2. A method as recited in claim 1 wherein said enriching step, said administering step, and said evaluating step collectively establish a first procedure, and wherein said method further comprises the steps of:

performing a subsequent procedure, said subsequent procedure being substantially the same as said first procedure; and comparing the concentration of $^{13}C$ in said first procedure with the concentration of $^{13}C$ in said subsequent procedure to determine the growth rate of the rapidly dividing cells in the in situ tissue.

3. A method as recited in claim 1 wherein said enriching step, said administering step, and said evaluating step collectively establish a first procedure, and wherein said method further comprises the steps of:

treating the malignancy indicated by the rapidly dividing cells;

performing a subsequent procedure, said subsequent procedure being substantially the same as said first procedure; and comparing the concentration of $^{13}C$ in the selected tissue in said first procedure with the concentration of $^{13}C$ in the selected tissue in said subsequent procedure to determine an efficacy of said treating step.

4. A method as recited in claim 1 wherein said nutrient contains glucose when the target tissue is non fatty.

5. A method as recited in claim 1 wherein said nutrient contains an amino acid when the target tissue is fatty.

6. A method as recited in claim 1 wherein said administering step is accomplished orally.

7. A method as recited in claim 1 wherein said administering step is accomplished intravenously.

* * * * *